United States Patent
Ho

(10) Patent No.: US 7,229,593 B1
(45) Date of Patent: Jun. 12, 2007

(54) PORTABLE VAPOR DIFFUSION COEFFICIENT METER

(75) Inventor: Clifford K. Ho, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 650 days.

(21) Appl. No.: 10/280,231

(22) Filed: Oct. 25, 2002

Related U.S. Application Data

(63) Continuation-in-part of application No. 10/152,597, filed on May 22, 2002.
(60) Provisional application No. 60/335,644, filed on Oct. 25, 2001.

(51) Int. Cl.
*B32B 5/02* (2006.01)
*B32B 27/04* (2006.01)
*B32B 27/12* (2006.01)
*G01N 7/00* (2006.01)
*G01N 21/00* (2006.01)

(52) U.S. Cl. .................. 422/83; 422/50; 422/68.1; 422/102; 422/103; 422/104; 73/1.01; 73/1.02; 73/152.41; 436/43; 436/52; 436/53; 436/181

(58) Field of Classification Search ............... 422/50, 422/68.1, 83, 102, 103, 104; 73/1.01, 1.02, 73/152.41; 436/43, 52, 53, 181
See application file for complete search history.

(56) References Cited

U.S. PATENT DOCUMENTS

| | | | | |
|---|---|---|---|---|
| 3,301,043 A | * | 1/1967 | Lyssy | 73/38 |
| 4,555,934 A | * | 12/1985 | Freeman et al. | 73/38 |
| 5,157,960 A | * | 10/1992 | Brehm et al. | 73/38 |
| 5,264,368 A | | 11/1993 | Clarke et al. | 436/3 |
| 5,278,501 A | * | 1/1994 | Guilfoyle | 324/303 |
| 5,361,625 A | * | 11/1994 | Ylvisaker | 73/38 |
| 5,513,515 A | * | 5/1996 | Mayer | 73/38 |
| 5,591,898 A | * | 1/1997 | Mayer | 73/38 |
| 5,627,329 A | * | 5/1997 | Krishnan et al. | 73/866 |
| 5,723,769 A | | 3/1998 | Barber et al. | 73/19.12 |
| 5,773,713 A | | 6/1998 | Barber et al. | 73/61.41 |
| 5,786,527 A | | 7/1998 | Tarte | 73/19.01 |
| 5,992,213 A | | 11/1999 | Tarte | 73/19.01 |
| 6,076,395 A | * | 6/2000 | Black et al. | 73/64.47 |

OTHER PUBLICATIONS

Ho and Hughes, "In-Situ Chemiresistor Sensor Package for Real-Time Detection of Volatile Organic Compounds in Soil and Groundwater", Jan. 30, 2002, pp. 23-34.

(Continued)

*Primary Examiner*—Brian Sines
(74) *Attorney, Agent, or Firm*—Robert D. Watson

(57) ABSTRACT

An apparatus for measuring the effective vapor diffusion coefficient of a test vapor diffusing through a sample of porous media contained within a test chamber. A chemical sensor measures the time-varying concentration of vapor that has diffused a known distance through the porous media. A data processor contained within the apparatus compares the measured sensor data with analytical predictions of the response curve based on the transient diffusion equation using Fick's Law, iterating on the choice of an effective vapor diffusion coefficient until the difference between the predicted and measured curves is minimized. Optionally, a purge fluid can forced through the porous media, permitting the apparatus to also measure a gas-phase permeability. The apparatus can be made lightweight, self-powered, and portable for use in the field.

50 Claims, 10 Drawing Sheets

OTHER PUBLICATIONS

Ho, Itamura, Kelley and Hughes, "*Review of Chemical Sensors for In-Situ Monitoring of Volatile Contaminants*", Mar. 2001 pp. 1-28.

Ho and Udell, "*An experimental investigation of air venting of volatile liquid hydrocarbon mistures from homogeneous and heterogeneous porous media*", Apr. 27, 1992, pp. 289-315.

Ho, "Analytical Inverse Model for Multicomponent Soil Vapor Extraction", Jun. 1998, pp. 504-507.

Ho, Hughes and Jenkins, "Waterproof Microsensor for In-Situ Monitoring of Volatile Compounds", Patent Application, pp. 1-39.

Ho, "Automated Monitoring and Remediation System for Volatile Subsurface Contaminants", Provisional Application, Jan. 23, 2002, pp. 1-10.

Ho, "Characterization Methods for Real-Time In-Situ Sensing of Volatile Contaminants", Provisional Application, Oct. 23, 2001, pp. 1-55.

Milligan, R. J. "Gas Diffusion in Porous Medi, Science" 1959, 130, 100-102.

Fuller, E. N. Schettler, P. D. and Giddings, J.C., "A Comparison of Methods for Predicting Gaseous Diffusion Coefficents," J. Gas Chromatography 1965, 2220227.

L. G. Wilson, L. G. Everett, S. J. Cullen, *Handbook of Vadose Zone Characterization and Monitoring*, Lewis Publishers, 1995 by CRC Press, Inc., Chapter 15, pp. 217-247.

\* cited by examiner

PORTABLE VAPOR DIFFUSION COEFFICIENT METER

CROSS-REFERENCE TO RELATED APPLICATIONS

This application is a continuation-in-part of U.S. application Ser. No. 10/152,597 filed May 22, 2002, "Waterproof Microsensor for In-Situ Monitoring of Volatile Compounds", by Clifford K. Ho, et al., which is incorporated herein by reference. This application claims the benefit of U.S. Provisional application Ser. No. 60/335,644 filed Oct. 25, 2001, "Characterization Methods for Real-Time In-Situ Sensing of Volatile Contaminants", by Clifford K. Ho, which is incorporated herein by reference. This application is related to co-pending application by Clifford K. Ho, "Automated Monitoring and Remediation System for Volatile Subsurface Contaminants Using In-Situ Sensors". This application is also related to application Ser. No. 10/280,258 by Clifford K. Ho, "Methods for Characterizing Subsurface Volatile Contaminants Using In-Situ Sensors", which issued as U.S. Pat. No. 7,003,405 on Feb. 21, 2006.

FEDERALLY SPONSORED RESEARCH

The United States Government has rights in this invention pursuant to Department of Energy Contract No. DE-AC04-94AL85000 with Sandia Corporation.

BACKGROUND OF THE INVENTION

This invention relates generally to the field of subsurface environmental remediation of underground sites contaminated with volatile compounds, and more specifically to equipment for measuring the effective diffusion coefficient and gas-phase permeability of a vapor moving through a porous media.

Volatile organic compounds (VOCs), also known as Non-Aqueous Phase Liquids (NAPLs), are the principal contaminants at many commercial and DOE sites. Some examples of VOCs include compounds such as aromatic hydrocarbons (e.g., benzene, toluene, xylenes); halogenated/chlorinated hydrocarbons (e.g., trichloroethylene (TCE), carbon tetrachloride); alcohols, ketones (e.g., acetone) and aliphatic hydrocarbons (e.g., hexane, octane). Other VCs of interest to groundwater protection include methyl tert-butyl ether (MTBE), other gasoline additives, toluene, and xylene (See 40 CFR 141.32 Primary Drinking Water Standards). Volatile contaminants can also include toxic chemicals, volatile pesticides, volatile fertilizers, buried volatile explosives, and organic compounds with low volatility. VC's can include gases or vapors other than volatile organic compounds, such as nitrogen oxide, nitrous oxide, carbon monoxide, carbon dioxide, hydrogen gas, and toxic gases, such as ammonia, chlorine, phosphonates, nerve gas (mustard, sarin, VX).

Tens of thousands of sites containing toxic chemical spills, leaking underground storage tanks, and chemical waste dumps require characterization and long-term monitoring (stewardship) to protect environmental resources (e.g., groundwater) and to determine when remedial measures are needed. Current methods are costly and time-intensive, and limitations in sampling and analytical techniques exist. For example, the Department of Energy (DOE) Savannah River Site requires manual collection of nearly 40,000 groundwater samples per year, which can cost between $100 to $1,000 per sample for off-site analysis (not including the cost of collecting the samples). Numerous commercial sites and applications, which include over two million underground storage tanks (e.g., at gas stations), also require monitoring to satisfy EPA requirements; as well as thousands of commercially contaminated sites that require characterization, monitoring, and/or remediation. Also, oil and natural gas fields currently take individual fluid samples manually from wells at a cost of nearly $250,000 per sample.

An important aspect of site characterization is understanding how vapors from volatile compounds move through porous soil, sand, cracked rock, etc, at various temperatures and moisture levels, and with or without a forced flow of a purge gas. A variety of computer codes exist that can model the flow of gases through a porous medium. However, the physical properties that are used in these codes, such as vapor diffusion coefficients and gas-phase permeabilities, are often unknown due to a lack of relevant experimental data.

Currently, there is no known portable device that can rapidly and accurately measure the effective vapor diffusion coefficient and gas-phase permeability for a vapor moving through a porous media, including advection by flow of a purge gas. A need exists, therefore, for an easily portable device that may be carried and used in the field, e.g., at an environmental restoration site. These sites commonly have core samples taken from both the contaminated and uncontaminated subsurface regions of the site. However, rather than mailing a large number of samples to an off-site laboratory, it would be faster and cheaper to analyze the samples on site using such a portable diffusion coefficient meter. Additionally, the properties of the subsurface media may change during the course of environmental remediation, that could require ongoing measurements of these properties.

A desirable aspect of in-situ monitoring is having the capability to not only detect the presence of contaminants, but to also characterize the contaminant in terms of its composition and location of its source. Traditional monitoring techniques require that the monitoring device be in the immediate vicinity of the contaminant to accurately detect and identify the contaminant location. Hence, a need exists for a characterization method that can identify the source's location using one or more in-situ sensors that are located relatively far away from the source.

If the effective vapor diffusion coefficient, D, is known, then analytical solutions may be used to estimate the distance from the in-situ sensor to the source. A portable diffusion coefficient meter could be used to measure the effective vapor diffusion coefficient, D, of actual core samples in the field, thereby increasing the accuracy and speed for which such a calculation (of the source distance) may be made. A triangulation method may be used with multiple in-situ sensors to determine the source location in two- and three-dimensions.

Current subsurface remediation methods use soil vapor extraction (SVE) techniques in the vadose zone (e.g., using a vacuum pump to pull vapors out of an extraction/exhaust well and/or air sparging techniques in the saturated zone e.g., pumping air down into a well to below the liquid level to force (i.e., advect) the flow of contaminant vapors through porous soil in the vadose zone towards an exhaust (i.e., exit) well or other opening).

The effectiveness and efficiency of these remediation techniques rely strongly on how quickly vapors from the volatile contaminant can diffuse or be advected through the various porous subsurface zones. The feasibility and economics of undertaking such a remediation effort depends strongly on the effective diffusion coefficients and gas-phase permeabilities of the porous media (which may be heterogenous). Knowledge of these properties during the project can help understand any unexpected changes in the vapor extraction rates, etc. Finally, the ability to efficiently conduct remedial measures in real-time (as needed) can improve public confidence in the ability of federal, state, and local governmental agencies to protect the environment and prevent contaminant migration away from these contaminated sites.

Against this background, the present invention was developed.

SUMMARY OF THE INVENTION

An apparatus for measuring the effective vapor diffusion coefficient of a test vapor diffusing through a sample of porous media contained within a test chamber. A chemical sensor measures the time-varying concentration of vapor that has diffused a known distance through the porous media. A data processor contained within the apparatus compares the measured sensor data with analytical predictions of the response curve based on the transient diffusion equation using Fick's Law, iterating on the choice of an effective vapor diffusion coefficient until the difference between the predicted and measured curves is minimized. Optionally, a purge fluid can forced through the porous media, permitting the apparatus to also measure a gas-phase permeability. The apparatus can be made lightweight, self-powered, and portable for use in the field.

BRIEF DESCRIPTION OF THE DRAWINGS

The accompanying drawings, which are incorporated in and form part of the specification, illustrate various examples of the present invention and, together with the detailed description, serve to explain the principles of the invention.

DETAILED DESCRIPTION OF THE INVENTION

The present invention relates to a portable apparatus for measuring effective vapor diffusion coefficients and gas-phase permeabilities of samples of porous media, such as soil, sand, clay, etc. The words "vapor" and "gas" are used interchangeably herein. Similarly, the acronym VOC, which stands for Volatile Organic Compound, is defined as encompassing inorganic volatile compounds (VCs) and other solvents, such as toxic chemicals, explosives, organic compounds having low volatility, and toxic gases.

The phrase "purge fluid" is defined herein to comprise a liquid, a gas, a vapor, a mixture of liquid and gas, a mixture of gas and suspended particles, or any combination thereof.

Figure 1:
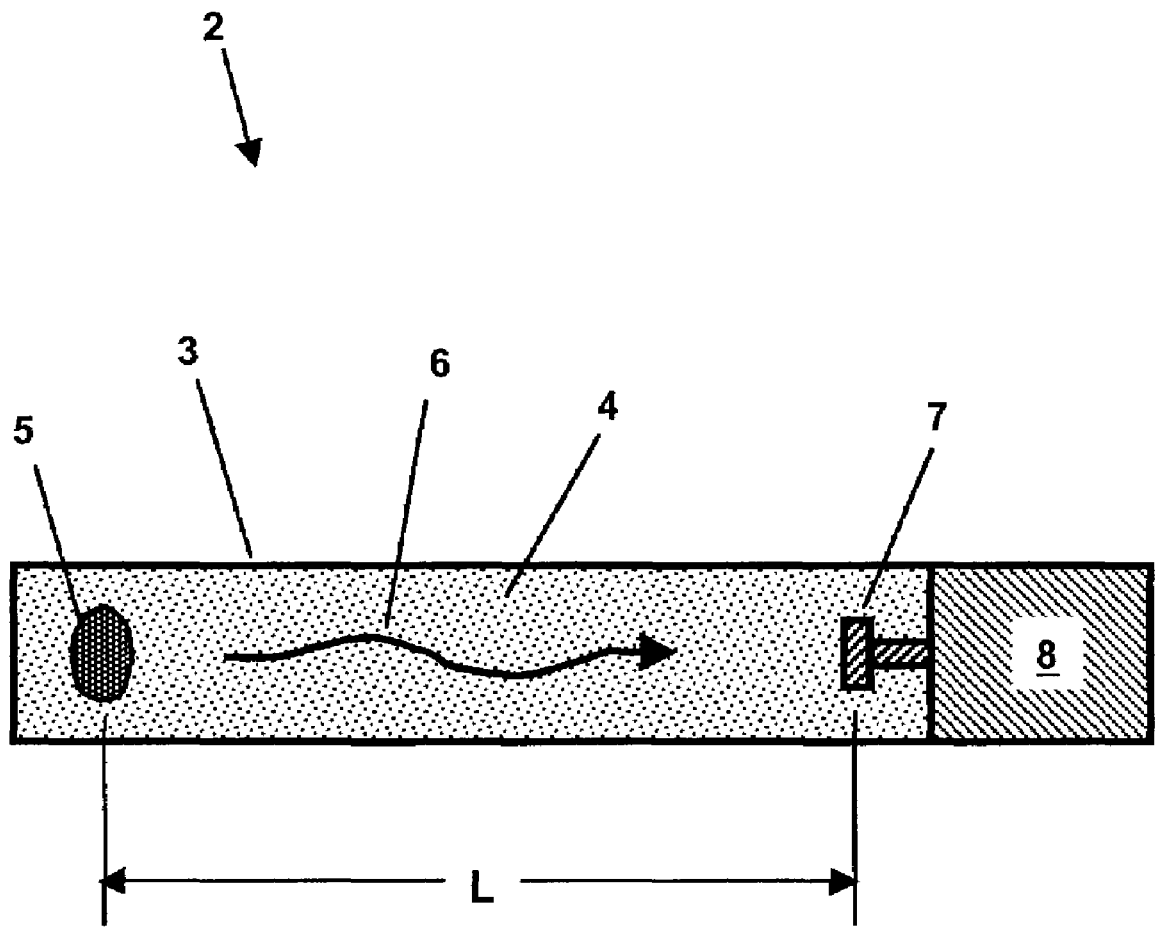
FIG. 1 shows a schematic cross-section view of a first embodiment of a vapor diffusion coefficient meter, according to the present invention.

FIG. 1 shows a schematic cross-section view of a first embodiment of a vapor diffusion coefficient meter, according to the present invention. Diffusion meter 2 comprises test chamber 3 that may be filled with a sample of porous media 4 to be tested. Means for introducing test vapor 5 may be located at one end of test chamber 3, and may comprise a cotton ball or other sponge-like material soaked with liquid NAPL or other volatile substance that readily emits test vapor 6. Test vapor 6 diffuses inside of test chamber 3 through porous media 4, eventually reaching sensor means 7, which is located at a distance, L, from the source of test vapor 5. Sensor means 7 is sensitive to the presence of test vapor 6, and produces a signal (in essentially real-time) that is proportional to the vapor's concentration. The signal generated by sensor means 7 is communicated to data processing means 8, which records the measured time-varying concentration of the test vapor and then calculates an effective vapor diffusion coefficient of the porous media. Data processing means 8 is an integral part of diffusion meter 2, for example, a small, dedicated microprocessor on a printed circuit board located inside of an enclosure housing the various components of the diffusion meter 2.

All of the components of diffusion meter 2 may be made small, compact, and lightweight using micro-sensors and dedicated microprocessor circuits. In this sense, diffusion meter 2 may be portable, e.g., weighing less than about 5 pounds, and where the length of the test chamber may be less than about 1 inch.

Sensor 7 may be a chromatographic, spectrographic, electrochemical, mass, or optical sensor. The in-situ sensor may be an ion mobility spectrometer (IMS) sensor, a catalytic bead sensor, a metal-oxide semiconductor sensor, a potentiometric sensor, an amperometric sensor, an acoustic wave sensor (e.g., a SAW sensor), a MEMS microcantilever sensor, a fiber optic sensor, a calorimetric sensor, and an infrared sensor (see Ho, C. K.; Itamura, M. T.; Kelley, M.; and Hughes, R. C. Review of Chemical Sensors for In-Situ Monitoring of Volatile Contaminants, *Sandia Report* 2001, SAND2001-0643, Sandia National Laboratories, Albuquerque, N. Mex., which is incorporated herein by reference).

An example of a suitable sensor 7 is described in related U.S. patent application, application Ser. No. 10/152,597 filed May 15, 2002, "Waterproof Microsensor for In-Situ Monitoring of Volatile Compounds", by Clifford K. Ho, et al., which is incorporated herein by reference. This in-situ chemical sensor can comprise a compact, rugged, waterproof housing (e.g., dimensions of 1-2 inches), with a gas-permeable membrane (such as GoreTex™) that contains one or more chemiresistor sensing elements that are sensitive to very low concentrations of VOC's (ppm's). The microsensor can include on-board heating elements to control the chemiresistors temperature, and can also include a pre-concentrator element to increase its sensitivity. Custom on-board ASIC circuits may be used to perform resistance calculations, condition data, measure temperatures, and control heater elements. This type of in-situ microsensor can have a response time scale on the order of seconds, which effectively is "real-time" compared to the typical time scale (hours/days/months) for subsurface diffusion of volatile contaminants.

Petrovend, Inc., of Hodgkins, Ill. (www.petrovend.com) manufactures a hydrocarbon vapor sensor probe that consists of a single chemiresistor sensor element (ADSISTOR™) mounted in a housing that has multiple openings through which vapors can freely flow. The probe's housing is not waterproof and, hence, cannot be placed in liquid-saturated soil, water, or other liquids contaminated with VOCs.

Geoprobe Systems, Inc. of Salina, Kans. (www.geoprobe-systems.com) manufactures a sampling device called a Geoprobe Membrane Interface Probe, is a cone penetrometer that has a gas permeable membrane covering an opening in the pointed tip (i.e., cone). The membrane selectively allows VOC gases in soil to diffuse through the membrane into the interior of the penetrometer. A gas supply & return tube located inside the penetrometer interfaces with the gas permeable membrane. A carrier gas is pumped through this tube to sweep up and carry VOCs (that have diffused through the membrane) up to a detector/analysis unit located on the surface. The Geoprobe Membrane Interface Probe performs in-situ sampling by pumping and/or drawing the diffused VOC vapor up to the surface via a carrier gas. However, the Geoprobe Membrane Interface Probe does not perform in-situ sensing or analysis, because sensing is performed by a remote detector/analysis unit located on the surface.

Many microsensor systems, such as portable hand-held spectrometers, gas chromatographs, catalytic bead sensors, and metal-oxide-semiconductor (MOS) sensors, utilize complex and sensitive electronic components, can use high temperature elements, and can require the flow of a carrier gas during operation to draw subsurface vapors up to the surface and into a chamber for sensing, none of which may be amenable to long-term in-situ monitoring applications. For example, the "Cyranose" hand-held electronic nose manufactured by Cyrano Sciences, Inc. (www.cyranosciences.com) is a chemiresistor-based microsensor that uses a pump to draw vapors into a sensing chamber. The Cyranose sensor unit, however, cannot be submerged in water for in-situ monitoring because the housing is not waterproof.

Polymer-based vapor absorbtion type sensors are attractive choices for use in a portable diffusion coefficient meter. Examples of these sensors include conductometric sensors such as chemiresistors, surface or thickness-shear mode acoustic wave (SAW) mass sensors, flexural plate wave mass sensors, and MEMS microcantilever mass sensors. Chemiresistors are a particularly simple type of chemical sensor whose electrical resistance changes in the presence of certain chemical vapors. Chemiresistors are easy to fabricate using well-known semiconductor fabrication techniques, may be made very small (<100 square microns), can operate at ambient temperatures, are passive devices (no pumps or valves are needed), and their resistance change may be read-out by a simple, low power (and low current) circuit that measures DC resistance. Also, chemiresistors are resistant to chemical poisoning (unlike catalytic sensors).

A common type of chemiresistor consists of a chemically sensitive, electrically insulating, organic, soluble polymer matrix that is loaded with a large volume (e.g., 20-40%) of electrically conductive metallic (e.g., gold, silver) or carbon particles to form a polymer-particle composite having a network of continuous electrically conductive pathways throughout the polymer matrix (i.e., host). To fabricate a chemiresistor, the polymer is mixed with a solvent (e.g., water, chlorobenzene, or chloroform) and sub-micron diameter carbon, silver, or gold particles (e.g., 20-30 nanometers) to make an "ink". Then, the resulting ink is deposited onto an insulating substrate as a thin film bridging across two (or more) spaced-apart thin-film electrodes, and then dried. A non-ionic surfactant can also be added to this mixture to chemically bond to the electrically conducting particles and thereby form steric barriers to prevent undesirable aggregation or agglomeration of these particles.

When chemical vapors of solvents, toxic chemicals, explosives, or VOCs come into contact with the polymer-particle composite, the polymer matrix absorbs the vapor(s) and swells. The swelling spreads apart the conductive particles, breaking some of the conductive pathways. This increases the electrical resistance across the two (or more) electrodes by an amount that is easily measured and recorded. The amount of swelling in steady-state, and, hence, the steady-state resistance change, is uniquely related to the concentration of the chemical vapor(s) in equilibrium with the chemiresistor. The resistance response is generally linear with increasing vapor concentration, but may become non-linear at high solvent concentrations when the percolation threshold of the polymer-particle composite is reached. The swelling process is generally reversible; hence the polymer matrix will shrink when the source of chemical vapor is removed (although some hysteresis can occur).

Chemiresistors generally should not be placed in direct contact with liquid VOCs because the polymer may be partially or completely dissolved by the liquid VOC, which may ruin the chemiresistor. Also, it is undesirable to have liquid water in contact with any electrical traces, leads or conductors used in the chemiresistor sensor, because of the potential for problems with short-circuiting and corrosion. Also, direct contact with water can cause the thin-film chemiresistor to detach from the substrate over time. Therefore, a waterproof, gas permeable membrane may be used to prevent liquid water or liquid VOCs from directly contacting the chemiresistors or exposed electronic components.

The polymer matrix used in chemiresistors generally absorbs multiple solvents having similar solubility parameters. See M. P. Eastman, R. C. Hughes, W. G. Yelton, A. J. Ricco., S. V. Patel and M. W. Jenkins, "Application of the Solubility Parameter Concept to the Design of Chemiresistor Arrays," *Journal of the Electrochemical Society*, Vol. 146, pp. 3907-3913, 1999. Since it is unlikely that any one specific polymer will be sensitive to only one particular VOC, an array of multiple chemiresistors containing a variety of polymer hosts is generally needed to provide accurate discrimination among multiple, interfering vapors (including water vapor).

Multiple chemiresistors have been fabricated side-by-side on a common substrate, such as a silicon wafer, where each chemiresistor has a different polymer matrix selected for high sensitivity to a particular VOC of interest. (See R. C. Hughes, et al., "Integrated Chemiresistor Array for Small Sensor Platforms," SPIE Proceedings, *Detection and Remediation Technologies for Mines and Minelike Targets V*, Vol 4038-62, pp. 519-529, Apr. 24-28, 2000). The more unknown VOCs there are, the greater the number of different polymers are needed to provide adequate discrimination. Hence, a fast and accurate identification technique is needed that can distinguish between multiple types of solvents (polar and non-polar), for both pure compounds and mixtures, over a wide range of concentrations, and in the presence of water vapor.

A common and obvious source of interfering vapors is water vapor (i.e., relative humidity) in the ambient environment. Water vapor affects the relative sensitivity of certain polymers to solvent vapors, and affects the patterns of responses obtained from arrays containing those polymers. To build a chemiresistor array that is capable of identifying the maximum number of possible analytes, the chemiresistors should be as chemically varied as possible, with at least one chemiresistor having significant sensitivity to water vapor.

Arrays of multiple chemiresistors have been successfully used to detect a wide variety of VOCs, including aromatic hydrocarbons (e.g., benzene), chlorinated solvents (e.g., trichloroethylene (TCE), carbon tetrachloride, aliphatic hydrocarbons (e.g., hexane, iso-octane), alcohols, and ketones (e.g., acetone)). See S. V. Patel, M. W. Jenkins, R. C. Hughes, W. G. Yelton, and A. J. Ricco., "Differentiation of Chemical Components in a Binary Solvent Vapor Mixture Using Carbon/Polymer Composite-Based Chemiresistors," *Analytical Chemistry*, Vol. 72, pp. 1532-1542, 2000.

Use of selective gas separation membranes can reduce the maximum number of different chemiresistors in an array since a VOC of particular interest may be selectively passed through the exterior wall of the package housing the chemiresistor array, while excluding other VOCs of lesser interest (e.g. via a selectively permeable membrane). For example, it would be useful to selectively pass chlorinated aliphatic hydrocarbons, but not aromatic hydrocarbons, through the sensor's enclosure.

To miniaturize the electronics that control and drive the chemiresistor arrays Application Specific Integrated Circuits (ASIC) may be integrated with the chemiresistors on a common substrate. The ASIC can perform a variety of functions, including measuring electrical resistance, conditioning data, sensing temperature, and controlling heater elements. (See R. C. Hughes, et al., "Integrated Chemiresistor Array for Small Sensor Platforms," SPIE Proceedings, *Detection and Remediation Technologies for Mines and Minelike Targets V*, Vol 4038-62, pp. 519-529, Apr. 24-28, 2000).

Chemiresistor arrays have also been integrated with a thin-film gas preconcentrator module located side-by-side on a common substrate (or facing each other in close proximity). See R. C. Hughes, S. V. Patel, and R. P. Manginell, A MEMS Based Hybrid Preconcentrator/Chemiresistor Chemical Sensor," Paper presented at the 198$^{th}$ Meeting of The Electrochemical Society, Phoenix, AX, Oct. 22-27, 2000. See also R. C. Hughes, R. P. Manginell, and R. Kottenstette, "Chemical Sensing with an Integrated Preconcentrator/Chemiresistor Array," Proceedings of Symposium on Chemical and Biological Sensors and Analytical Methods II, Meeting of The Electrochemical Society, San Francisco, Calif., Sep. 2-7, 2001.

The preconcentrator module works by slowly adsorbing VOC vapors into a thin layer of sorbtive material (i.e., "phase") over a sustained period of time, and then quickly releasing a concentrated puff of the VOC gas by rapidly heating the sorbent using an underlying resistance heater element. The adjacent chemiresistor array is then exposed to a highly concentrated amount of the VOC, which effectively improves the limit of detection of VOCs by factors of 10-1000 times (e.g., from ppm to ppb).

Data analysis techniques for analyzing the resistance response of chemiresistor sensors (or other microchemical sensors) can use the method of Principal Components Analysis (PCA) to identify statistical trends that can distinguish individual VOCs (See, e.g., Lewis and Freund, Sensor Arrays for Detecting Analytes in Fluids, U.S. Pat. No. 5,951,846). However, at high vapor concentrations PCA methods cannot generally be used because the chemiresistor's response becomes non-linear when the percolation threshold is approached.

The non-linear response, however, may be analyzed using pattern recognition techniques (in addition to linear responses). These techniques work by using neural network methods or by comparing the resulting chemical signatures with calibration (i.e., training) sets using advanced pattern recognition software, such as the Visual Empirical Region of Influence (VERI) technique. See G. C. Osbourn, et al., Visual-Empirical Region-of-Influence Pattern Recognition Applied to Chemical Microsensor Array Selection and Chemical Analysis," *Acc. Chem. Res*. Vol. 31, pp. 297-305, 1998. See also U.S. Pat. No. 6,304,675 to Osbourn, et al., "Visual Cluster Analysis and Pattern Recognition Methods". The "VERI" pattern recognition algorithm performs a similar operation to human vision by analyzing the clustering of the unknown data points with training data from known VOCs.

Figure 2:
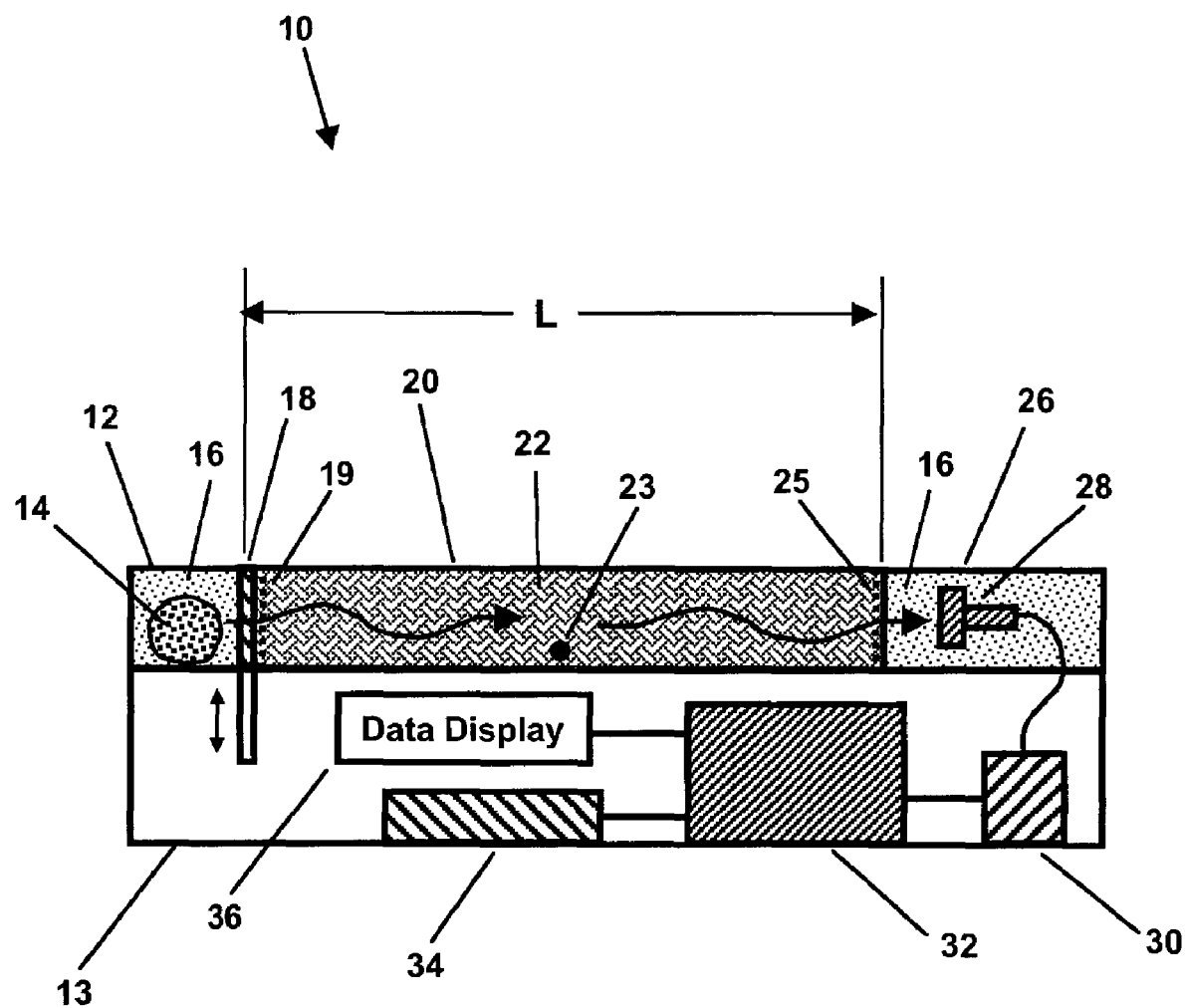
FIG. 2 shows a schematic cross-section view of a second embodiment of a vapor diffusion coefficient meter, according to the present invention.

FIG. 2 shows a schematic cross-section view of a second embodiment of a vapor diffusion coefficient meter, according to the present invention. Diffusion meter 10 comprises a source chamber 12 for holding vapor source 14, which emits test vapor 16. Vapor source 14 may comprise, for example, a cotton ball or other sponge-like material loaded or soaked with a volatile liquid contaminant (e.g., NAPL) that emits vapors 16. Test chamber 20 may be filled with porous test media 22. Movable partition 18, such as an automatic or manually-operated gate valve with compliant seals, may be used to separate source chamber 12 from test chamber 20. Chemical sensor 28 may be housed inside detector chamber 26. The length, L, of test chamber 20 is approximately equal to the length of porous test media 22 in this embodiment. Alternatively, test chamber 20 may comprise mechanical means for adjusting the length of porous media 22 to be less than the length of test chamber 20, such as a plunger or piston with penetrations for vapor to flow through (not shown). Data logger 30 may records data generated by sensor 28, which may be processed by data processor 32. Power supply 34 may provide electrical power to data processor 32 and other internal components, as needed. Power supply 34 may comprise a battery pack, which may be recharged in the field by a solar cell panel (not shown). Alternatively, AC power may be used. Data processor 32 processes the sensor data and calculates the desired results (e.g., effective vapor diffusion coefficient, gas-phase permeability, etc.), optionally storing the results in internal memory (not shown), and/or displaying the results on data display 36, which may be a LED display. Data and calculated results stored in the internal memory may be outputted on a strip-chart recorder, or made available to be downloaded via standard removable memory media (e.g., discs, cards, sticks, tapes, etc.), or transferred via electronic link or wireless telemetry means to a PC, Palm Pilot™, Internet connection, video monitor, etc., or combinations thereof. Test chamber 20 may comprise a hollow cylinder made of a relatively gas impermeable material, e.g., glass, metal, ceramic, plastic, stainless steel, or other materials well-known in the art.

Diffusion meter 10 may be oriented with respect to gravity so that the direction which vapor 16 travels through test chamber 12 is oriented substantially parallel to the ground, so that gravity has no effect on the vapor transport mechanism. Alternatively (not illustrated), diffusion meter 10 may be positioned at an inclined angle (including up to vertical) by using an adjustable support structure (not shown). Meter) 10 may be tilted so that source chamber 12 is positioned lower than detector chamber 26, so that test vapor 16 has to rise against the force of gravity to reach detector chamber 26. Alternatively, device 10 may be tilted so that source chamber 12 is positioned higher than detector ion chamber 26, so that test vapor 16 falls along with the force of gravity towards detector chamber 26. These alternative orientations can be used to assess the influence of gravity on the apparent effective diffusion coefficient for a particular analyte and porous material.

The aspect ratio (i.e., length/diameter, if chamber 12 is a cylinder) of test chamber 12 may be chosen to be sufficiently long and thin so that test vapor 16 diffuses essentially in a single direction towards sensor 28, producing essentially one-dimension vapor diffusion, which eases the requirements for calculating the effective vapor diffusion coefficient. An aspect ratio greater than about five may be used to produce essentially one-dimensional flow.

The length, L, of test chamber 20 may be on the order of centimeters, for example, to reduce the measurement time. Alternatively, the length, L, of test chamber 20 may be adjusted to different lengths to accommodate, for example, porous materials having different grain sizes. Shorter test lengths, L, would provide faster test results, however, the accuracy and repeatability of the calculated results (i.e., diffusion coefficient, gas permeability) would not be as good as when using longer test lengths, L, which would allow more time to collect data and to "stretch out" the response curve. Test chamber 20 may optionally comprise a bellows-type construction and/or flexible material that can easily accommodate large variations in the test length.

Referring still to FIG. 2, an embodiment of portable device 10 may additionally comprise first and second gas permeable means 19, 25 for preventing test media 22 from spilling or falling into test/detection chambers 12, 26, respectively, while at the same time permitting vapor 16 to pass through the gas permeable means essentially unhindered. An example of gas permeable means 19, 25 can comprise a porous membrane, such as expanded PTFE (e.g., GoreTex®), fine mesh or screen, porous filter paper or filter media, porous ceramic disk or plate (e.g., alumina), microporous metal sheet (i.e., laser drilled), where the openings are small enough to contain test media 22, while allowing vapor molecules 16 to pass through.

Diffusion meter 10 may optionally contain means (not shown) for measuring the temperature, pressure, and relative humidity in some, or all, of chambers 12, 20, and 26, and in multiple locations inside of test chamber 20. Diffusion meter 10 may be thermally insulated (especially chambers 12, 20, and 26) to prevent large temperature variations during testing. One or more heating elements (not shown) may be used to control the internal temperatures of chambers 12, 20, and 26. Individual heating elements may be used to independently control the temperatures of each individual chamber, which may be different from each other, depending on particular test requirements.

Sensor 28 may be easily removable, so that it may be easily switched out as it ages, maintained, cleaned, and/or replaced if damaged. The specific type of sensor used may be selected to optimally detect the particular analyte or volatile compound being studied.

Test chamber 20 may be filled with air or other gas, or, alternatively, evacuated. Optionally, test chamber 20 may be easily removed and replaced/re-inserted, so that other samples of test media 22 may be rapidly tested by simply switching out the filled test chamber 20 with another filled test chamber of the same length. This eliminates the need to first clean out a test chamber before a new measurement may be taken; i.e., it may be cleaned while another test is proceeding.

Test chamber 20 may be located adjacent a dessicant to reduce or remove any water from porous media 22. Alternatively, electric heating means (e.g., heater tape wrapped around a cylindrical test chamber 20), may be used to heat porous media 22 and bake out any water.

A first embodiment of a method of measuring the effective vapor diffusion coefficient using the embodiment of meter 2 illustrated in FIG. 1 may comprise the following steps: a) placing a sample of porous media 4 inside test chamber 3; b) introducing a source 5 of test vapor 6 near the entrance of test chamber 4; c) measuring with sensor 7 the time-varying concentration of test vapor 6 at a location where the test vapor has diffused a distance, L, through the sample of porous media 4; d) recording the measured time-varying concentration of test vapor 6; and e) using integral data processor 8 to calculate an effective vapor diffusion coefficient of porous media 4.

With respect now to FIG. 2, the following method steps may be employed, in no specific order, comprising: filling test chamber 20 with test media 22; loading volatile contaminant sample 14 into test chamber 20; calibrating and adjusting the baseline of sensor 28; applying power to, and initializing, data logger 30 and data processor 32; measuring ambient conditions (e.g., temperature, pressure, relative humidity); opening and closing movable partition 18; collecting, recording, processing data from sensor 28; and displaying/storing/transmitting calculated results, for example, on data display 36. After initialization has been completed, the test sequence may be started by opening first movable partition 18 to allow test vapor 16 to move from source chamber 12 into test chamber 20. Test vapor 16 diffusing through test media 22 and enters detector chamber 26, where it is detected by sensor 28. Movable partition 18 may comprise a motor-driven gate valve (not shown), with compliant seals, or may comprise a camera-style iris mechanism. Partition 18 and 24 may be opened by pressing a "start button" (not shown) on device 10, which also initiates the collecting and recording of sensor data by data logger 30. After a sufficiently long period of time has elapsed (to be discussed later), the recording of sensor data terminates and movable partition 18 may be closed, thereby terminating the test.

Method of Analysis

When the vapor concentration in test chamber 20 is zero (or, essentially very small) at the beginning of the test (i.e., at time=0), then diffusion of the test vapor 16 from vapor source 14 in chamber 12, through porous media 22, to sensor 28 (e.g., a chemiresistor sensor) produces a time-dependent "breakthrough" response curve of the time-varying vapor concentration that has a well-known shape. The shape of the experimental/measured breakthrough curve can subsequently be analyzed using the following methods to calculate an effective vapor diffusion coefficient and/or the gas-phase permeability of porous test media 22.

The following simplified one-dimensional mathematical model describes the diffusive mass transfer of vapor in a homogenous, isotropic porous media. The model predicts the time-dependent vapor-concentration breakthrough curve at the sensor's location. The porous media is assumed to be effectively isotropic and homogenous; as represented by an effective (e.g., averaged) vapor diffusion coefficient and gas-phase permeability. Non-homogeneous and/or non-isotropic test media 22 may be tested in diffusion meter 10, however, the calculated results will reflect the "effective" properties averaged along the length of test chamber 20.

A mass balance yields the following governing differential equation for one-dimensional diffusion of vapor in a porous medium:

$$\frac{\partial C}{\partial t} = D \frac{\partial^2 C}{\partial x^2} \quad (1)$$

where C is vapor concentration [kg/m$^3$], D is the effective vapor diffusion coefficient in porous media [m$^2$/s], t is the time [s], and x is the distance [m] from the source (e.g., NAPL). It should be noted that the term "effective vapor diffusion coefficient" (D) is used synonymously here with "vapor diffusivity." This term, D, in Equation (1) equals the ratio of the effective diffusion coefficient used in Fick's Law (to calculate a mass flux) and the gas-phase porosity that arises from the storage term (left-hand side) of Equation (1). If gas-solid partitioning occurs, this term (D) will also include partitioning coefficients that provide retardation to the diffusive flux.

The initial and boundary conditions that are used by data processor 32 in diffusion meter 10 are:

$$C(x, t=0) = C_i \quad (2)$$

$$C(x=0, t) = C_s \quad (3)$$

$$\frac{\partial C(x=L, t)}{\partial x} = 0 \quad (4)$$

where $C_i$ is the initial vapor concentration in the domain, $C_s$ is the vapor concentration at the source, and L is the distance between the source and the sensor. The concentration, C, may be normalized as C' between 0 and 1 as follows:

$$C'(x, t) = \frac{C(x, t) - C_i}{C_s - C_i} \quad (5)$$

The one-dimensional solution for the normalized vapor concentration evaluated at the sensor location (x=L) may be expressed as follows:

$$C' = 1 - \frac{4}{\pi} \sum_{n=0}^{\infty} \frac{(-1)^n}{2n+1} \exp\left(-\frac{D(2n+1)^2 \pi^2 t}{4L^2}\right) \quad (6)$$

The normalized time-dependent concentration in Eq. (6) may be plotted as a function of time to yield a time-varying vapor concentration breakthrough response curve that has a shape defined by the effective diffusion coefficient, D, and the distance between the sensor and the contaminant source, L. Since the separation distance, L, is known, then the effective diffusion coefficient, D, may be inversely determined by comparing the predicted response to the measured data. Data processor 32 may digitize and normalize the sensor data recorded by data logger 30, and then use a statistical analysis program to statistically compare the measured and predicted data. Data processor 32 may use, for example, a least-squares regression analysis method to obtain a best fit between the normalized time-dependent concentration from Eq. (6) and the normalized measured test data, by iteratively adjusting the value of the effective vapor diffusion coefficient, D, used in Ea. (6), until sufficiently acceptable agreement has been reached (e.g., when the residual error between the measured and predicted data is less than 1%). In other words, the iterative inverse solution procedure continues until the predicted curve best matches the measured curve, at which point the last value of the estimated coefficient is selected as being the calculated coefficient that is reported by the apparatus. Other inverse mathematical techniques may be used to determine a single value of the effective vapor diffusion coefficient, D, that best matches the experimental data. Optionally, choosing a good initial guess for the unknown variable (D) can significantly reduce the analysis time.

An example of one method to select a good initial guess for the effective diffusion coefficient, D, is to use the following equation (see Millington, R. J. Gas Diffusion in Porous Media. *Science* 1959, 130, pp. 100-102.), which is incorporated herein by reference:

$$D = \phi_a^{4/3} \left(\frac{\phi_a}{\phi_t}\right)^2 D^0 = (1 - S_l)^{10/3} \phi_t^{4/3} D^0 \quad (7)$$

where $\phi_a$ is the air-filled porosity, $\phi_t$ is the total porosity, $S_l$ is the liquid saturation, and $D^0$ is the binary gas-phase diffusion coefficient in air given in Fuller, E. N.; Schettler, P. D. and Giddings, J. C., "A Comparison of Methods for Predicting Gaseous Diffusion Coefficients," *J. Gas Chromatography* 1965, pp. 222-227, which is incorporated herein by reference. This equation estimates the effective diffusion coefficient used in Fick's Law for a partially saturated porous media. The effective vapor diffusion coefficient in porous media is typically less than the binary diffusion coefficient in air because of obstructions caused by liquid and solid phases in the porous media that increase the tortuosity and reduce the available area for diffusion.

It should noted that the estimate in Equation (7) does not represent the "effective diffusion coefficient" (or "vapor diffusivity") used in Equation (1) exactly, because it neglects the gas-phase porosity and partitioning coefficients (if gas-solid partitioning occurs) contributed by the storage term (left-hand side) of Equation (1). Nevertheless, Equation (7) provides a convenient "first-guess" when parameters such as the gas-phase porosity and partitioning coefficients are uncertain. If these parameters are known, the effective diffusion coefficient in Equation (7) would be divided by these storage coefficients to obtain the effective diffusion coefficient used in Equation (1).

The examples of a diffusion meter shown in FIGS. 1 and 2, according to the present invention, may be used to generate and record a time-varying "breakthrough" curve for the test analyte of interest without problems caused by advective flow or disturbances in the pressure, which would alter the estimation of the diffusion coefficient. Because the temperature and pressure may be controlled, the diffusion meter essentially provides a purely diffusive environment. Additionally, if the vapor diffusion coefficient is already known (for example, from other tests or references), then any retardation of the transient breakthrough curve due to vapor-solid partitioning may be estimated.

The overall diffusion coefficient calculated using the inverse procedure described above and equation (6) is equal to the ratio of the effective diffusion coefficient divided by a retardation factor. If there is no gas-to-solid phase partitioning in the porous media, then the retardation factor equals one. Consequently, if the effective diffusion coefficient is known (and entered by the user), then the retardation factor (i.e., coefficient) may be calculated by dividing the overall calculated diffusion coefficient by the user-entered effective diffusion coefficient.

Other formulas may be used to estimate an effective vapor diffusion coefficient, D, for a porous media with consideration of increased tortuosity, reduced area caused by the porous media, and possible retardation caused by partitioning of the vapor onto the solid phase.

Experimental Demonstration

Figure 3:
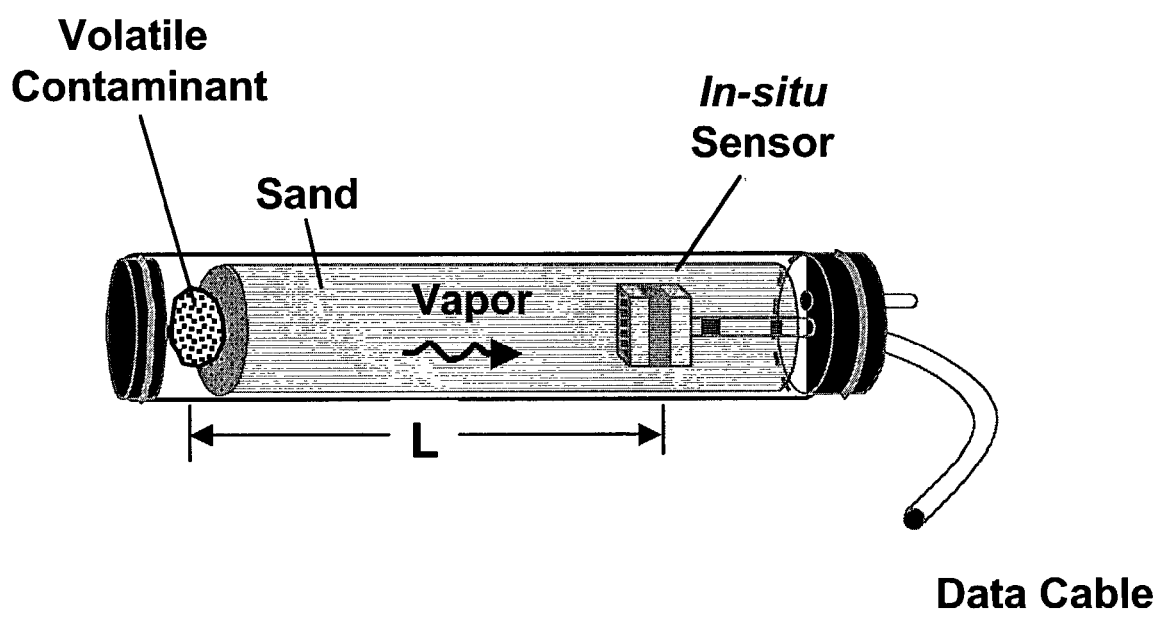
FIG. 3 shows a schematic of the experimental setup.

One-dimensional column experiments were performed to test the use of a chemiresistor-type sensor in a simulated geologic environment and to demonstrate the one-dimensional analysis method derived above. FIG. 3 shows a schematic of the experimental setup. The experiment consisted of a sand-filled glass (borosilicate) column sealed by an in-situ chemiresistor sensor at one end of the column and a contaminant source (saturated iso-octane NAPL) at the other end. The sand used in the experiments was dry and sorted using 10-20 mesh sieves. The sensor package was fit into a custom-made adaptor that provided an air-tight seal between the sensor package and the 5-cm diameter tube. The NAPL contaminant was placed into a piston-like reservoir that also provided an air-tight seal at the other end of the tube. Small amounts of liquid iso-octane (several milliliters), sufficient to saturate the column with iso-octane vapor, was introduced into the reservoir via soaked cotton balls placed at one end of the test column. A steel mesh/screen covering the cotton balls in the reservoir prevented direct contact between the sand and the liquid iso-octane. The sensor was surrounded by the sand in this experimental setup.

The chemiresistor sensor was connected by cable to an Agilent 34970A data logger, which was connected to a Dell Optiplex PC. After the iso-octane saturated contaminant was placed inside the tube at time=0, the electrical resistance of the chemiresistor sensor was periodically recorded to monitor the diffusion of iso-octane vapors through the sand to the sensor. As derived in the previous section, the sand provides additional resistance to mass diffusion (as compared to vapor diffusion in air), and the "breakthrough curve" has a diffusive shape dependent on the separation distance between the sensor and contaminant, as well as the effective diffusion coefficient. Two separate experiments were conducted using separation distances of 20 cm and 36 cm, respectively.

The chemiresistor sensor was calibrated before the experiment to different concentration exposures to iso-octane. The calibration curves were used to convert the measured electrical resistance changes of the chemiresistors to vapor-phase iso-octane concentrations. The concentrations measured by the sensor were then normalized to the maximum concentration, and results were plotted as a function of time. Finally, the measured time-varying vapor concentrations were compared to the predicted one-dimensional analytical solutions of diffusion transport from Eq. (6).

To use the analytical solution in Eq. (6), the effective diffusion coefficient and separation distance between the sensor and contaminant source term are needed. Eq. 7 provides an expression for the effective diffusion coefficient, where the binary diffusion coefficient for iso-octane at 100 kPa and 22° C. was estimated as $6.5 \times 10^{-6}$ m$^2$/s (see Fuller, E. N., et al., supra), the liquid saturation was zero, and the sand porosity had an average measured porosity of 0.35.

Experimental Results

Figure 4:
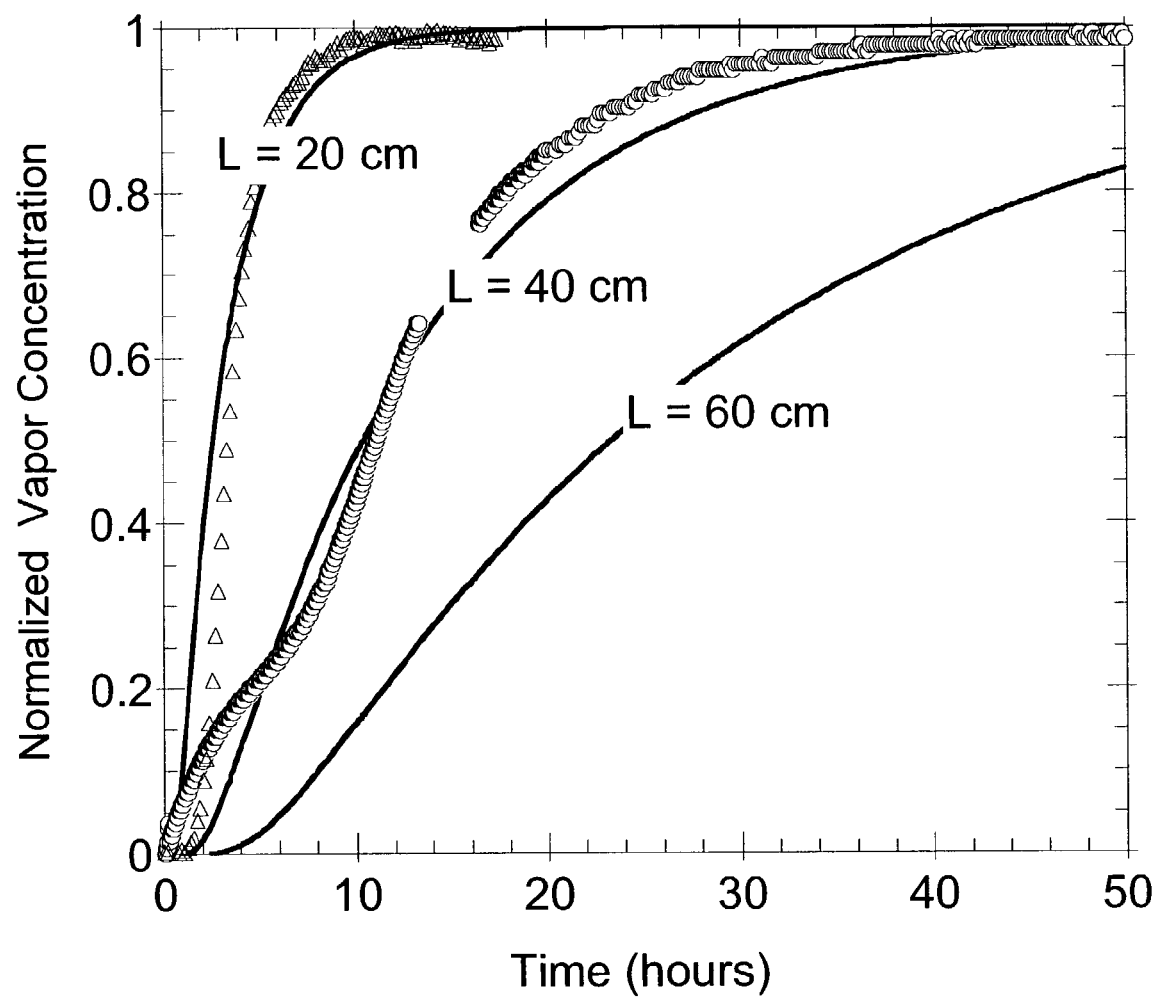
FIG. 4 shows the experimental results of the one-dimensional column experiments, along with one-dimensional analytical solutions predicted for three different assumed distances (i.e., 20, 40, and 60 cm) to demonstrate how the location of the contaminant may be estimated using an iterative/inverse approach.

FIG. 4 shows the experimental results of the one-dimensional column experiments, along with one-dimensional analytical solutions predicted for three different assumed distances (i.e., 20, 40, and 60 cm) to demonstrate how the location of the contaminant may be estimated using an iterative/inverse approach. The data points are shown as symbols, and the predictions from the analytical solution are shown as solid lines for the three assumed distances. Results indicate that the measured time-varying concentrations for the 20 cm experiment align most closely with the predicted results that assumed a distance, L, of 20 cm. Similarly, the measured concentrations for the 36 cm source distance experiment best match the predicted results that assumed a distance of 40 cm. Slight deviations in the experimental breakthrough curves may be due to additional factors not considered in the model, such as adsorption of the vapors onto the sand, which would tend to flatten and stretch-out the breakthrough curves. Nevertheless, a simple visual inspection of the experimental and theoretical breakthrough curves may be used to estimate the distance to the source-term location with acceptable accuracy. More rigorous statistical methods using regression techniques (e.g., lease-squares minimization) may be used to better quantify the location based on the analytical predictions.

Figure 5:
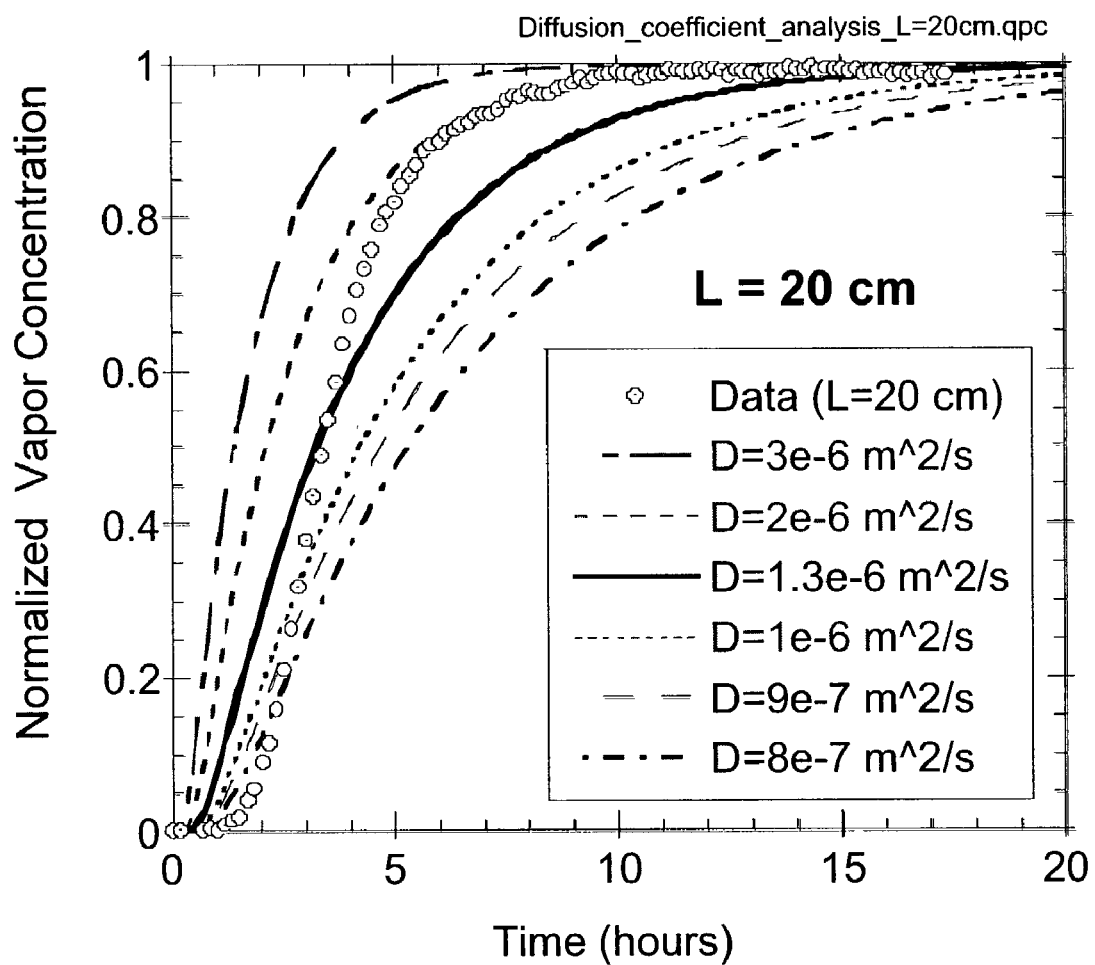
FIG. 5 shows the experimental results of the one-dimensional column experiment for L=20 cm.
Figure 6:
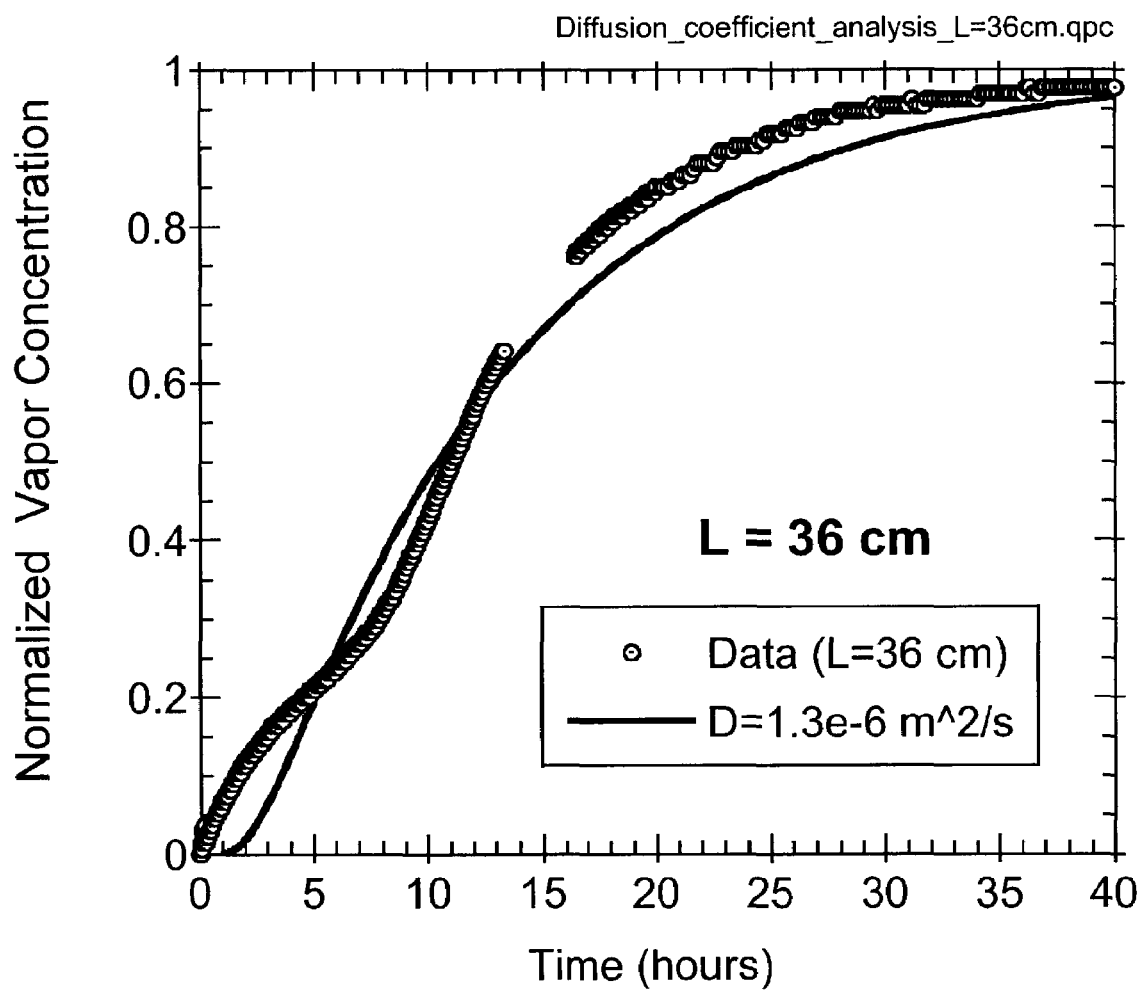
FIG. 6 shows the experimental results of the one-dimensional column experiment for L=36 cm.

FIGS. 5 and 6 show the same experimental results for L=20 cm and L=36 cm, respectively, as presented above in FIG. 4. However, in these two figures, the predicted response curves using eq. (6) used a fixed, known value for the separation distance L (either 20 or 36 cm), and the effective diffusion coefficient, D, was assumed to be different values, ranging from 0.8 E-6 to 3.0 E-6 m$^2$/s. In both FIGS. 5 and 6, it can be seen that using an assumed value of 1.3 E-6 for the diffusion coefficient produced the best matching curve to the measured data points (circles). The process of choosing the best curve that fits the experimental can be automated by comparing the two curves and calculating the residual error between them, and then using an iterative method to pick the best value of D that eventually minimizes the overall residual error, such as a least-squares minimization technique.

Figure 7:
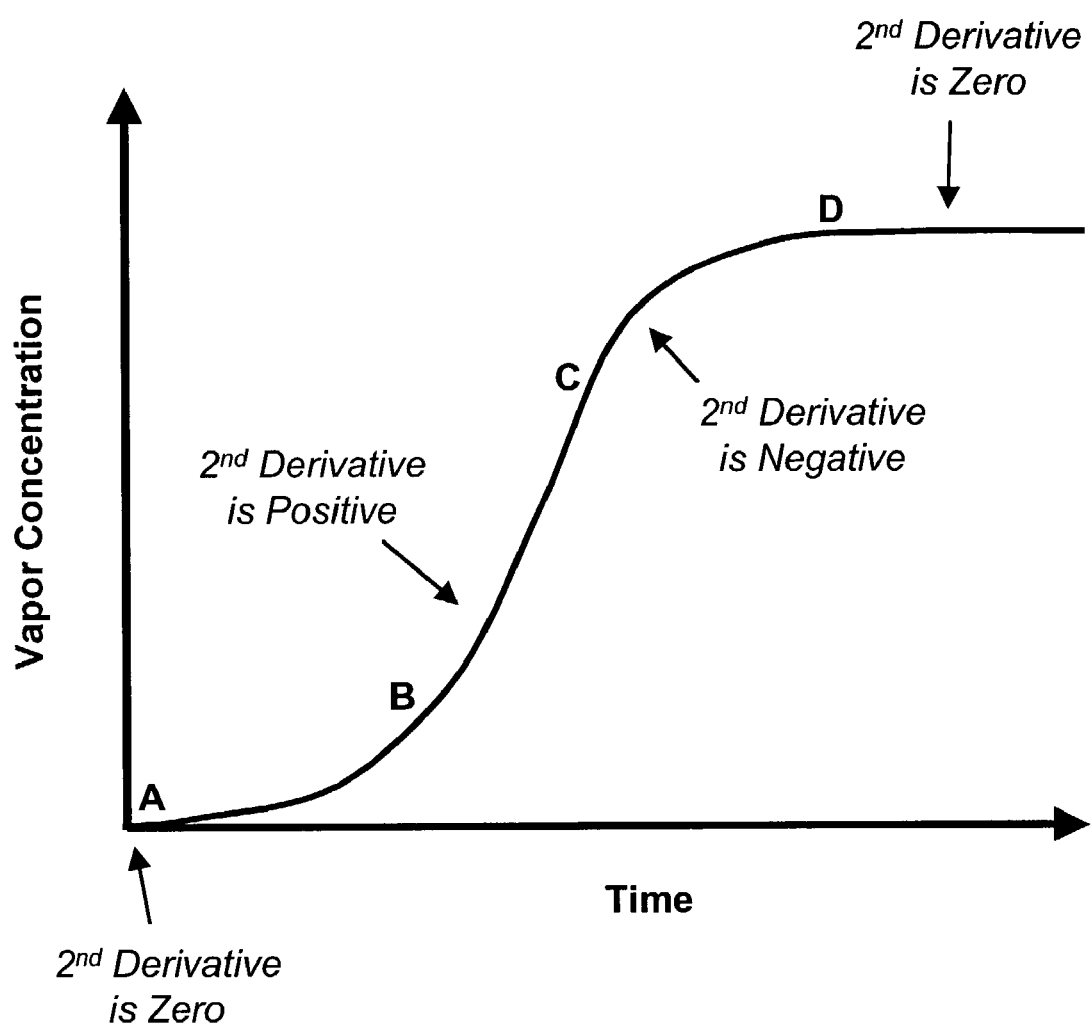
FIG. 7 illustrates schematically the characteristic shape of a time-varying vapor concentration breakthrough (i.e., transient response) curve, for vapor diffusing through a porous media.

FIG. 7 illustrates schematically the characteristic shape of a time-varying vapor concentration breakthrough (i.e., transient response) curve, for vapor diffusing through a porous media. The first derivative with respect to time (i.e., slope) of the response curve is essentially zero at the beginning of the test (point 'A'), positive during the transient portion (points 'B' and 'C'), and returns to near zero when a steady-state concentration is eventually reached (point 'D'). The second derivative with respect to time (i.e., curvature) of the response curve goes through the following characteristic regimes: (A) initially zero when the concentration is a flat line; (B) positive when the concentration begins to increase at the detector; (C) transition to negative as the increase in concentration begins to slow and reach an asymptotic steady state value; and (C) approaches zero when the saturated (steady-state) vapor concentration is reached.

The self-contained data processor of the present invention (see, for example, the embodiments shown in FIGS. 1 and 2) may utilize the information derived from the measured vapor response curve by calculating and inspecting the first and second derivatives of the response curve (i.e., the curvature), as discussed above, and illustrated in FIG. 7. Data processor 32 may be programmed with various data analysis algorithms to identify the various inflection points (A, B, C, and D) of the measured response, and make appropriate decisions regarding the test sequence. Using these inflection points, the data analysis algorithm can automatically determine when enough data has been collected. For example, the test may be stopped when the calculated first derivative falls below a pre-selected threshold value, indicative of reaching a steady-state concentration (i.e., point 'D'). Alternatively, or in conjunction, the test may be stopped when the calculated second derivative changes from a positive number to a negative number, indicative of approaching a steady-state concentration (i.e., point 'C'). Using the decision algorithm based on the second derivative will generally reduce the measurement time, however, with the possibility that the calculated result will not be as robust (i.e., as compared to a test which runs for a longer period of time). Diffusion meter 10 may use a light and/or sound alarm/indicator (not shown) to signal when the diffusion coefficient calculation has been completed.

If these characteristic regimes are not identified by data processor 32, an error message may be posted to data display 136 (or, alternatively, via a pre-programmed verbal notification through a small loudspeaker) to indicate that the sample should be purged and re-run.

After enough data is collected, an optimization algorithm is performed, which minimizes the difference between the predicted and measured values. The light/sound alarm may be turned on, and the result posted to an LED display and stored in memory. Both the light/sound alarm and LED display may be turned off after a prescribed amount of time.

Figure 8:
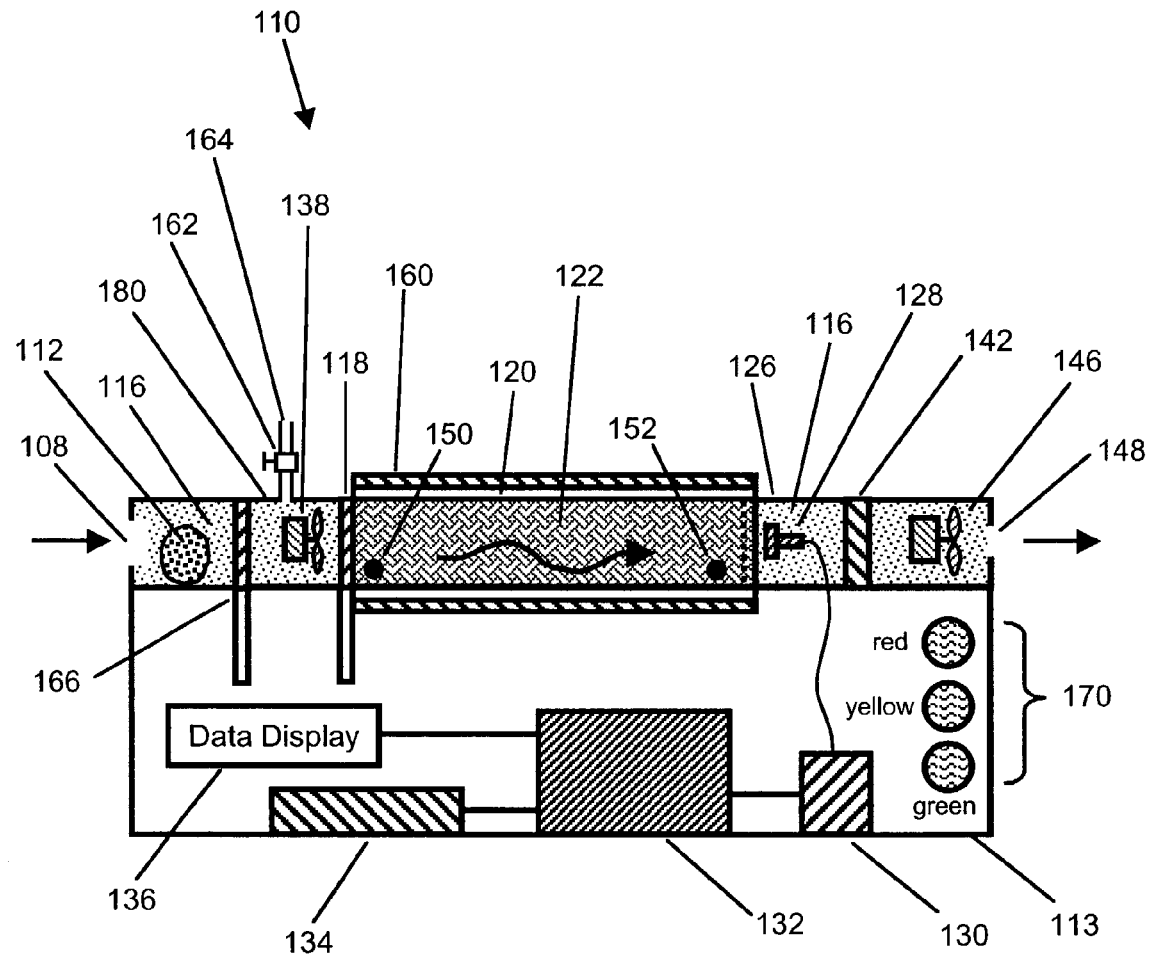
FIG. 8 shows a schematic cross-section view of a third embodiment of a vapor diffusion coefficient meter, according to the present invention.

FIG. 8 shows a schematic cross-section view of a third embodiment of a vapor diffusion coefficient meter, according to the present invention. Diffusion meter 110 may additionally comprise upstream pump 138 and, optionally, downstream pump 146, for actively forcing the flow of a purge fluid (e.g., gas, vapor, or liquid) through test chamber 20. Pumps 138 and/or 146 may comprise a fan, compressor, vacuum pump, or liquid pump, as is well-known in the art. Movable partitions 166 and 118 may be used to control the rate of purge fluid flowing. The purge fluid (e.g., air, oxygen, ozone, air plus ozone, water, nitrogen, helium, and combinations thereof) may be used to purge test vapor 116 from test chamber 122 (and, possibly, detector chamber 126) after each test, which would allow multiple runs to be performed in rapid succession using the same vapor source 14. For example, when movable partition 166 is closed and movable partition 118 is open, then gas inlet tube 164 and control valve 162 may be opened to admit air into upstream pump chamber 180 for forcing through test chamber 120 via upstream pump 138. Alternatively, the purge fluid may be forced past vapor source 112, advecting vapors 116, which are forced through the porous test media 22 to simulate various active remediation process, e.g., air sparging, or soil vapor extraction (SVE). Environmental sensors 150 and 152 may be located at one (or both) ends of porous media 22 to measure the temperature, pressure, relative humidity, or combinations thereof, inside of test chamber 20, as well as the pressure drop across test chamber 20 from entrance to exit. Optionally, flowmeter 142 may be used to measure the flow rate of the purge fluid. Test chamber 120 may be surrounded by heating jacket 160 and insulation (not shown) for heating and controlling porous media 122 inside of test chamber 120. Alternatively, heating elements may be placed just on one side of test chamber 120. Heating jacket 160 may be used to evaporate water from porous media 122 prior to, during, or after a measurement test. The embodiment shown in FIG. 8 also illustrates the use of colored status indicator lights 170, e.g., red, yellow, and green.

By measuring both the pressure drop across test chamber 120 and the flow rate of the purge fluid (e.g., air), the gas-phase permeability of the porous test material may be calculated by using Darcy's Law, which is given by:

$$Q = \frac{kk_r}{\mu} \frac{P_1 - P_2}{L} A \qquad (8)$$

where Q is the measured flow rate [m³/s], k is the intrinsic permeability [m²], $k_r$ is the relative permeability to account for phase interferences [-], m is the dynamic viscosity of air [N-s/m²], $P_1$ is the pressure measured by the upstream pressure transducer [N/m²], $P_2$ is the pressure measured by the downstream pressure transducer [N/m²], L is the distance between the two pressure transducers [m], and A is the cross-sectional area of the flow [m²].

If we assume that the porous medium is dry ($k_r$=1), then the gas-phase permeability may be calculated as follows:

$$k = \frac{Q\mu L}{(P_1 - P_2)A} \qquad (9)$$

All of the parameters on the right-hand side can either be prescribed or measured. The dynamic viscosity of air could be programmed into the diffusion meter at various temperatures (e.g., a temperature-dependent function could be used).

If advective processes are also occurring in the test chamber due to purge fluid flow creating pressure gradients, more complex solutions to the advection-diffusion equation may be used to predict the transient response of the contaminant breakthrough curve at the sensor's location.

The advection-dispersion equation may be written as follows, assuming constant porosity, diffusion coefficient, and liquid saturation:

$$\frac{\partial C}{\partial t} = D\nabla^2 C - \nabla \cdot (vC) \qquad (10)$$

where C is the concentration [kg/m³], t is time [s], D is the effective diffusion/dispersion coefficient, and v is the gas velocity vector defined by Darcy's Law. Inverse/iterative solutions like those described above may be used to solve Eq. (10) by minimizing the difference between predicted and measured sensor data.

Figure 9:
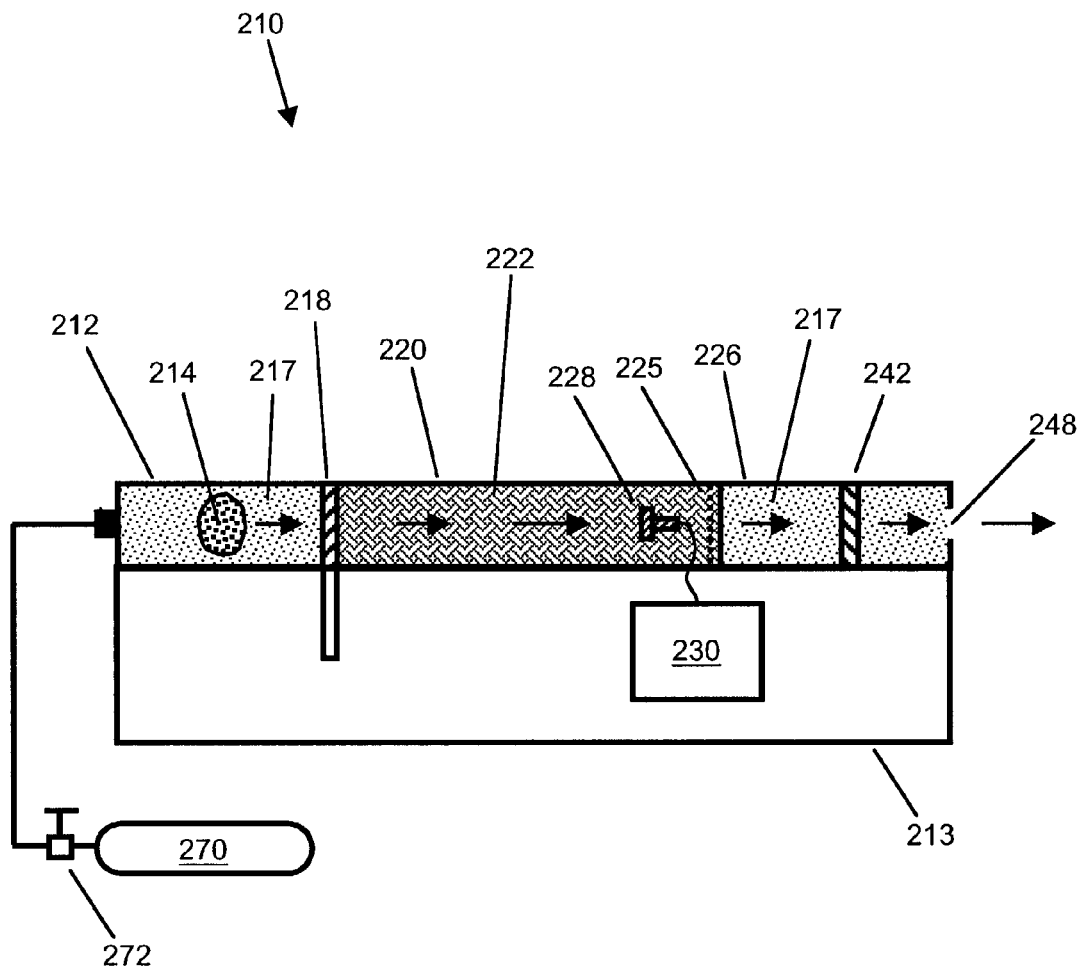
FIG. 9 shows a schematic cross-section view of a fourth embodiment of a vapor diffusion coefficient meter, according to the present invention.

FIG. 9 shows a schematic cross-section view of a fourth embodiment of a vapor diffusion coefficient meter, according to the present invention. Diffusion meter 210 may additionally comprise purge gas supply means for supplying purge gas to source chamber 212, for example, gas bottle 270 and control valve 272. Alternatively, sensor 228 may be located inside of test chamber 220, surrounded by porous media 222.

Figure 10:
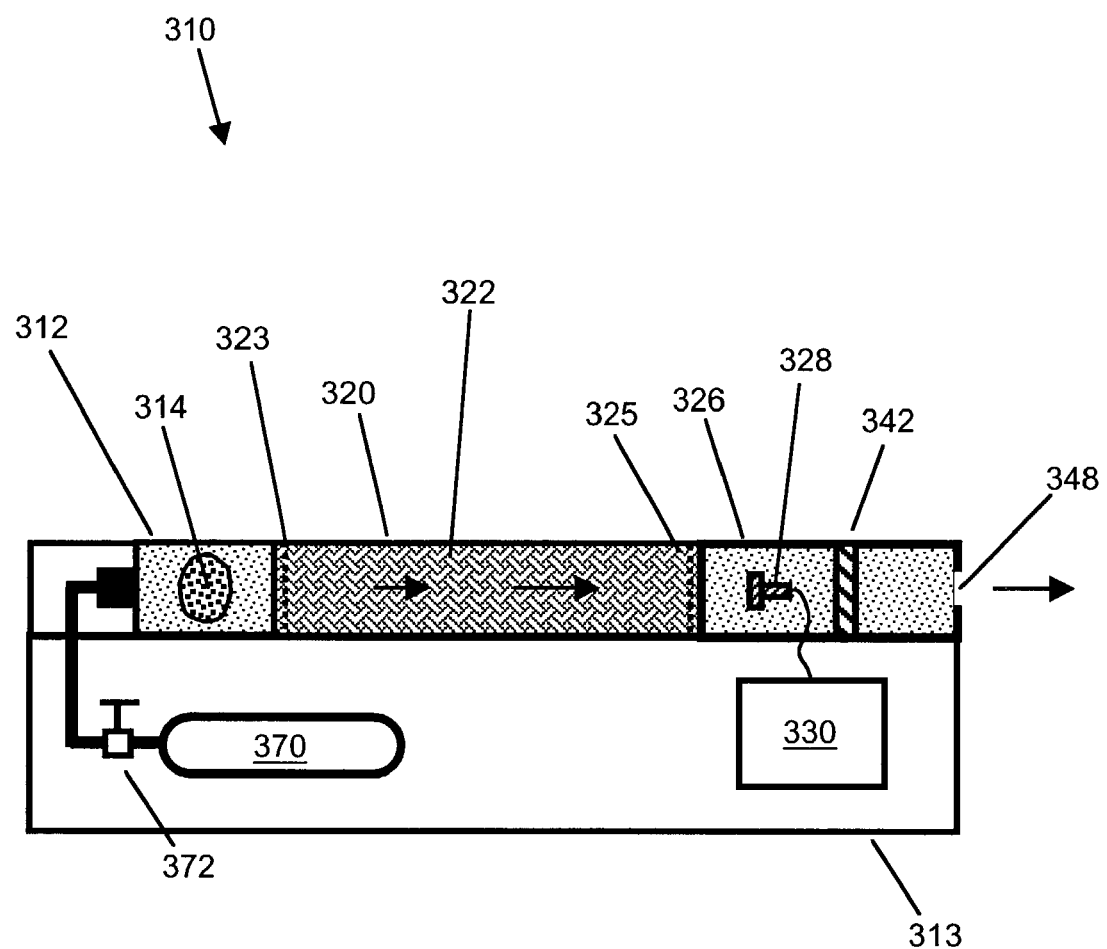
FIG. 10 shows a schematic cross-section view of a fifth embodiment of a vapor diffusion coefficient meter, according to the present invention.

FIG. 10 shows a schematic cross-section view of a fifth embodiment of a vapor diffusion coefficient meter, according to the present invention. Purge gas supply bottle 370 and control valve 373 are located inside of diffusion meter 310.

The particular examples discussed above are cited to illustrate particular embodiments of the invention. Other applications and embodiments of the apparatus and method of the present invention will become evident to those skilled in the art.

The actual scope of the invention is defined by the claims appended hereto.

What is claimed is:

1. An apparatus for measuring an effective vapor diffusion coefficient of a test vapor diffusing through a porous test media, comprising:
   a test chamber comprising a hollow cylinder made of a gas impermeable material, for holding a sample of porous test media having a length=L, the chamber comprising an entrance and an exit;
   source means, fluidically connected to the entrance of the test chamber, for introducing test vapor into the test chamber;
   sensor means, fluidically connected to the exit of the test chamber, for measuring time-varying concentrations of test vapor after the test vapor has diffused the distance, L, through the sample of porous test media disposed inside the test chamber; and
   data processing means for recording measured time-varying concentrations of test vapor and for calculating an effective vapor diffusion coefficient of the test vapor diffusing through the porous test media; and further
   wherein said source means comprises a source chamber connected to the entrance of the test chamber for holding a source of a volatile substance, and further comprising a movable partition disposed in-between the source chamber and the entrance to the test chamber for controlling the flow of vapor from the source chamber into the test chamber.

2. The apparatus of claim 1, wherein said sensor means comprises a detector chamber connected to the exit of the test chamber, and further comprising a sensor disposed within said detector chamber.

3. The apparatus of claim 1, further comprising one or more screens disposed at the entrance and exit of the test chamber to prevent particulates of the porous test media from falling out of the test chamber.

4. The apparatus of claim 1, further comprising a battery-powered supply for supplying power to the apparatus.

5. The apparatus of claim 1, wherein the data processing means comprises computer program means for calculating an effective vapor diffusion coefficient according to the following method, which comprises:
   a) measuring and recording time-varying concentrations of test vapor at a location where test vapor has diffused a distance, L, through a sample of porous test media contained within the test chamber;
   b) generating a measured response curve based on the measured time-varying vapor concentrations;
   c) estimating an effective vapor diffusion coefficient, D;
   d) predicting the time-varying concentration C' using the effective vapor diffusion coefficient, D, estimated in step c), and using the known distance, L, by using an analytical solution for one-dimensional diffusion of vapor from a fixed source;
   e) generating a predicted response curve based on the predicted concentrations;
   f) normalizing the measured response curve;
   g) comparing the normalized predicted and measured response curves;
   h) repeating steps d) through h) as many times as necessary, each time adjusting the estimated effective vapor diffusion coefficient, D, until the shape of the normal-ized predicted response curve best matches the shape of the normalized measured response curve; and
   i) selecting the final value of the estimated effective vapor diffusion coefficient to be the calculated effective vapor diffusion coefficient, D, from step h).

6. The apparatus of claim 5, wherein analytical solution used in step d) comprises using the following equation for the normalized vapor concentration evaluated at the sensor location (x=L):

$$C' = 1 - \frac{4}{\pi} \sum_{n=0}^{\infty} \frac{(-1)^n}{2n+1} \exp\left(-\frac{D(2n+1)^2 \pi^2 t}{4L^2}\right).$$

7. The apparatus of claim 5, wherein the method further comprises using a least-squares regression statistical analysis to estimate the effective vapor diffusion coefficient.

8. The apparatus of claim 1, wherein the sensor means comprises a chemiresistor sensing element.

9. The apparatus of claim 1, wherein the sensor means comprises a sensor housed in a waterproof housing comprising a gas permeable membrane.

10. The apparatus of claim 1, further comprising means for heating a sample of porous test media disposed inside the test chamber.

11. The apparatus of claim 1, wherein the sensor means is disposed inside of the test chamber.

12. The apparatus of claim 1, wherein the test chamber is removable from the apparatus.

13. The apparatus of claim 1, further comprising means for measuring one or more environmental parameters selected from the group of temperature, pressure, and relative humidity, and combinations thereof.

14. The apparatus of claim 1, wherein the apparatus is portable and weighs less than about five pounds.

15. The apparatus of claim 1, wherein the test chamber comprises a stainless steel cylinder with threaded ends for coupling to another threaded cylinder or threaded end cap.

16. The apparatus of claim 1, further comprising adjustable support means attached to the apparatus for holding the apparatus at a inclined angle with respect to gravity, wherein the inclined angle includes a vertical angle.

17. The apparatus of claim 1, further comprising means for adjusting the length of a sample of porous test media disposed inside of the test chamber.

18. The apparatus of claim 1, further comprising:
   a source chamber for holding the source of test vapor, comprising an entrance aperture;
   an upstream pump chamber disposed in-between the source chamber and the test chamber;
   a detector chamber connected to the exit of the test chamber, comprising the sensor means and an exit aperture;
   an upstream pump disposed inside the upstream pump chamber for forcing the flow of a purge fluid towards the entrance of the test chamber;
   a first movable partition connecting together the source chamber and the upstream pump chamber; and
   a second movable partition connecting together the upstream pump chamber and the test chamber.

19. The apparatus of claim 18, further comprising a flowmeter for measuring the flow rate of purge fluid through the test chamber.

20. The apparatus of claim 18, further comprising a downstream pump disposed inside the detector chamber for forcing the flow of a purge fluid away from the exit of the test chamber.

21. The apparatus of claim 18, further comprising upstream sensor means disposed near the entrance of the test chamber for measuring one or more environmental parameters selected from the group of temperature, pressure, and relative humidity, and combinations thereof; and wherein the apparatus further comprises downstream sensor means disposed near the exit of the test chamber for measuring one or more environmental parameters selected from the group of temperature, pressure, and relative humidity, and combinations thereof.

22. The apparatus of claim 18, further comprising means for heating a sample of porous test media disposed inside of the test chamber to a sufficiently high temperature for a sufficiently long period to evaporate water from the porous test media.

23. The apparatus of claim 18, wherein the upstream pump chamber comprises means for admitting air into the upstream pump chamber.

24. The apparatus of claim 1, further comprising purge gas supply means, fluidically connected to the entrance of the test chamber, for providing a flow of purge gas through the test chamber.

25. The apparatus of claim 24, wherein the purge gas supply means is contained within the apparatus.

26. A method of measuring an effective vapor diffusion coefficient of a test vapor diffusing through a porous test media, by using an apparatus comprising,
 a test chamber comprising a hollow cylinder made of a gas impermeable material, for holding a sample of porous test media having a length=L, the chamber having an entrance and an exit;
 source means, fluidically connected to the entrance of the test chamber, for introducing test vapor into the test chamber;
 sensor means, fluidically connected to the exit of the test chamber, for measuring time-varying concentrations of test vapor after the test vapor has diffused the distance, L, through the sample of porous test media disposed inside the test chamber; and
 data processing means for recording measured time-varying concentrations of test vapor and for calculating an effective vapor diffusion coefficient of the test vapor diffusing through the porous test media;
wherein the method of measuring comprises;
 a) placing a sample of porous test media inside the test chamber;
 b) introducing a source of test vapor near the entrance of the test chamber;
 c) using the sensor means to measure time-varying concentrations of the test vapor at a location where the test vapor has diffused a distance, L, through the sample of porous test media;
 d) recording the measured time-varying concentrations of the test vapor; and
 e) using the data processing means to calculate an effective vapor diffusion coefficient of the test vapor diffusing through the porous test media using the recorded sensor data; and
wherein calculating the effective vapor diffusion coefficient in step e) comprises:
 f) generating a measured response curve based on the measured time-varying vapor concentrations;
 g) estimating an effective vapor diffusion coefficient D;
 h) predicting the time-varying concentration C' using the effective vapor diffusion coefficient, D, estimated in step h), and using the known distance, L, by using an analytical solution for one-dimensional diffusion of vapor from a fixed source;
 i) generating a predicted response curve based on the predicted concentrations;
 j) normalizing the measured response curve;
 k) comparing the normalized predicted and measured response curves;
 l) repeating steps h) through l) as many times as necessary, each time adjusting the estimated effective vapor diffusion coefficient, D, until the shape of the normalized predicted response curve best matches the shape of the normalized measured response curve; and
 m) selecting the final value of the estimated effective vapor diffusion coefficient to be the calculated effective vapor diffusion coefficient, D, from step l).

27. The method of claim 26, wherein the analytical solution used in step c) comprises the following equation for the normalized vapor concentration evaluated at the sensor location (x=L):

$$C' = 1 - \frac{4}{\pi} \sum_{n=0}^{\infty} \frac{(-1)^n}{2n+1} \exp\left(-\frac{D(2n+1)^2 \pi^2 t}{4L^2}\right).$$

28. The method of claim 26, further comprising using a least-squares regression statistical analysis to determine the effective vapor diffusion coefficient, D.

29. The method of claim 26, further comprising exposing the sensor means to the sample of porous test media disposed inside of the test chamber for a period of time sufficiently long to establish a steady-state, baseline vapor concentration, before introducing the source of test vapor at the entrance of the test chamber in step b).

30. The method of claim 26, further comprising heating of the porous test media inside of the test chamber.

31. The method of claim 26, further comprising flowing a purge fluid through the test chamber.

32. The method of claim 31, further comprising removing the test vapor from the porous test media by flowing the purge fluid through the test chamber.

33. The method of claim 31, further comprising advecting test vapor from the test vapor source by flowing the purge fluid past the test vapor source.

34. The method of claim 31, wherein the purge fluid comprises a fluid selected from the group of air, oxygen, ozone, air plus ozone, water, steam, nitrogen, helium, and combinations thereof.

35. The method of claim 31, comprising measuring the flow rate of the purge fluid; and further comprising measuring the pressure drop across the test chamber.

36. The method of claim 31, further comprising using a pressurized gas bottle to supply a purge gas to the apparatus.

37. The method of claim 31, further comprising using an upstream pump located upstream of the test chamber to force the flow of purge fluid towards the entrance of the test chamber.

38. The method of claim 31, further comprising using a downstream pump located downstream of the test chamber to force the flow of purge fluid away from the exit of the test chamber.

39. The method of claim 35, further comprising using Darcy's Law to calculate the gas-phase permeability of the porous test media during steady-state flow conditions of the flowing purge fluid.

40. The method of claim 26, further comprising calculating a first derivative with respect to time of the measured time-varying vapor concentrations, and then stopping the measurement test when the calculated first derivative falls below a pre-selected threshold value, indicative of reaching a steady-state concentration of the test vapor.

41. The method of claim 26, further comprising calculating a second derivative with respect to time of the measured time-varying vapor concentrations, and then stopping the measurement test when the calculated second derivative changes from a positive number to a negative number, indicative of approaching a steady-state concentration of the test vapor.

42. The method of claim 26, wherein a user enters a fixed value of an effective vapor diffusion coefficient into the data processor of the apparatus, thereby allowing the data processor to subsequently calculate a retardation factor caused by partitioning of test vapor onto solid phases in the porous test media.

43. The apparatus of claim 1, wherein the sensor means comprises at least one sensor selected from the group consisting of an ion mobility spectrometer (IMS) sensor, a catalytic bead sensor, a metal-oxide semiconductor sensor, a potentiometric sensor, an amperometric sensor, an acoustic wave sensor, a SAW sensor, a MEMS microcantilever sensor, a fiber optic sensor, a calorimetric sensor, an infrared sensor, a chemiresistor, thickness-shear mode acoustic wave mass sensor, and a flexural plate wave mass sensor.

44. The apparatus of claim 1, wherein the sensor means comprises an array of at least two chemiresistors, integrated with a thin-film gas preconcentrator module side-by-side on a common substrate or facing each other in close proximity.

45. The apparatus of claim 1, wherein the sensor means has a response time scale on the order of seconds.

46. The apparatus of claim 1, wherein the cylindrical test chamber has a length/diameter ratio greater than about five.

47. The apparatus of claim 1, wherein the cylindrical test chamber has a length, L, of from 20 to 60 cm.

48. The apparatus of claim 3, wherein the one or more screens is selected from the group consisting of a porous membrane, expanded PTFE, a fine mesh, porous filter paper, filter media, a porous ceramic disk or plate, a porous alumina disk or plate, and a microporous metal sheet; wherein the openings in the screen are small enough to contain the porous test media, while allowing vapor molecules to pass through.

49. The apparatus of claim 1, wherein the test chamber is thermally insulated.

50. The apparatus of claim 1, further comprising individual heating elements for heating the source chamber and the test chamber to a temperature that may be the same, or different, from each other.

* * * * *